United States Patent
Stöbich

(10) Patent No.: US 9,744,355 B2
(45) Date of Patent: Aug. 29, 2017

(54) WIRELESS AUDIO SIGNAL MONITOR OUTPUT FOR HEARING IMPLANT SYSTEM

(75) Inventor: Bernhard Stöbich, Axams (AT)

(73) Assignee: MED-EL ELEKTROMEDIZINISCHE GERAETE GmbH, Innsbruck (AT)

( * ) Notice: Subject to any disclaimer, the term of this patent is extended or adjusted under 35 U.S.C. 154(b) by 829 days.

(21) Appl. No.: 13/424,524

(22) Filed: Mar. 20, 2012

(65) Prior Publication Data

US 2012/0245654 A1    Sep. 27, 2012

Related U.S. Application Data

(60) Provisional application No. 61/467,453, filed on Mar. 25, 2011.

(51) Int. Cl.
 *A61N 1/00* (2006.01)
 *A61N 1/36* (2006.01)
 *H04R 25/00* (2006.01)

(52) U.S. Cl.
 CPC ......... *A61N 1/36032* (2013.01); *H04R 25/30* (2013.01); *H04R 25/554* (2013.01); *H04R 2225/67* (2013.01)

(58) Field of Classification Search
 CPC .. A61N 1/0541; A61N 1/36032; H04R 25/30; H04R 25/554; H04R 2225/025; H04R 2225/67; H04R 2225/021
 USPC ....................................... 607/55–57
 See application file for complete search history.

(56) References Cited

U.S. PATENT DOCUMENTS 4,532,930 A *   8/1985  Crosby et al. ............... 607/57
 2010/0070000 A1 * 3/2010  Litvak et al. .................. 607/57

* cited by examiner

*Primary Examiner* — Mallika D Fairchild
(74) *Attorney, Agent, or Firm* — Sunstein Kann Murphy & Timbers LLP

(57) ABSTRACT

An external processor device for a hearing implant system is described. An audio signal processor is coupled to an audio input providing an electrical audio input signal and develops a corresponding implant stimulation signal output. A stimulation signal transmitter is coupled to the signal processor and receives the implant stimulation signal for transmission to an implanted portion of the hearing implant system. The device includes an audio bypass mode which provides the audio input signal to the stimulation signal transmitter for transmission.

4 Claims, 2 Drawing Sheets

WIRELESS AUDIO SIGNAL MONITOR OUTPUT FOR HEARING IMPLANT SYSTEM

This application claims priority from U.S. Provisional Patent 61/467,453, filed Mar. 25, 2011, incorporated herein by reference.

TECHNICAL FIELD

The present invention relates to hearing implant systems and specifically an arrangement for checking proper audio input signals to such systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain.

Hearing is impaired when there are problems in the ability to transduce external sounds into meaningful action potentials along the neural substrate of the cochlea 104. In some cases, hearing impairment can be addressed by a hearing implant system such as a cochlear implant that electrically stimulates auditory nerve tissue with small currents delivered by multiple electrode contacts distributed along an implant electrode.

FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing, and produces a stimulation pattern (based on the extracted audio information) that is sent through an electrode lead 109 to an implanted electrode array 112 which penetrates into the cochlea 104 through a surgical opening called a cochleostomy. Typically, this electrode array 112 includes multiple electrode contacts 110 on its surface that deliver the stimulation signals to adjacent neural tissue of the cochlea 104 which the brain of the patient interprets as sound. The individual electrode contacts 110 may be activated sequentially or simultaneously in one or more contact groups.

Parents or guardians of non-cooperative hearing implant users (e.g. children) sometimes want to be able to check whether or not the hearing implant system or at least part of it (e.g. the external audio processor) is working properly. That is quite difficult technically. One existing method that allows a subjective evaluation of the front-end audio processing is listening to the sensed audio signal (e.g. from a microphone, telecoil, external audio input, FM system, etc.) by a normal hearing person via a headphone or loudspeaker. This does not allow a detailed diagnosis of the entire hearing implant system, but it is a simple method that allows a normal hearing person to answer the question whether or not a proper audio signal is picked up by the audio processor of the hearing implant system. Defective microphones, telecoils or external audio inputs as well as misadjusted or defective FM systems can be detected, thus making troubleshooting easier.

Existing external processors for hearing implant systems usually provide the internal electric audio signal via mechanical connectors on the outside of the device. These connectors may be directly accessible or may become accessible after the external processor device is disassembled; for example, when the battery pack is detached from the control unit. But the sensed electrical audio signal is not normally available for listening so by a normal hearing person.

SUMMARY

Embodiments of the present invention are directed to an external processor device for a hearing implant system. An audio signal processor is coupled to an audio input providing an electrical audio input signal and develops a corresponding implant stimulation signal output. A stimulation signal transmitter is coupled to the signal processor and receives the implant stimulation signal for transmission to an implanted portion of the hearing implant system. The device includes an audio bypass mode which provides the audio input signal to the stimulation signal transmitter for transmission.

For example, the electrical audio input signal may be a microphone signal, a telecoil signal, an external audio signal, or a digital audio signal. The hearing implant system may include a cochlear implant (CI) system, an auditory brainstem implant (ABI) system, or a middle ear implant (MEI) system.

DETAILED DESCRIPTION

Various embodiments of the present invention are directed to techniques to make internal electric analog or digital audio signals externally available from within an external hearing implant processor by using the existing wireless (e.g. inductive) link normally used for transmitting the electrical stimulation signals to the implanted part of the hearing implant system.

Figure 1:
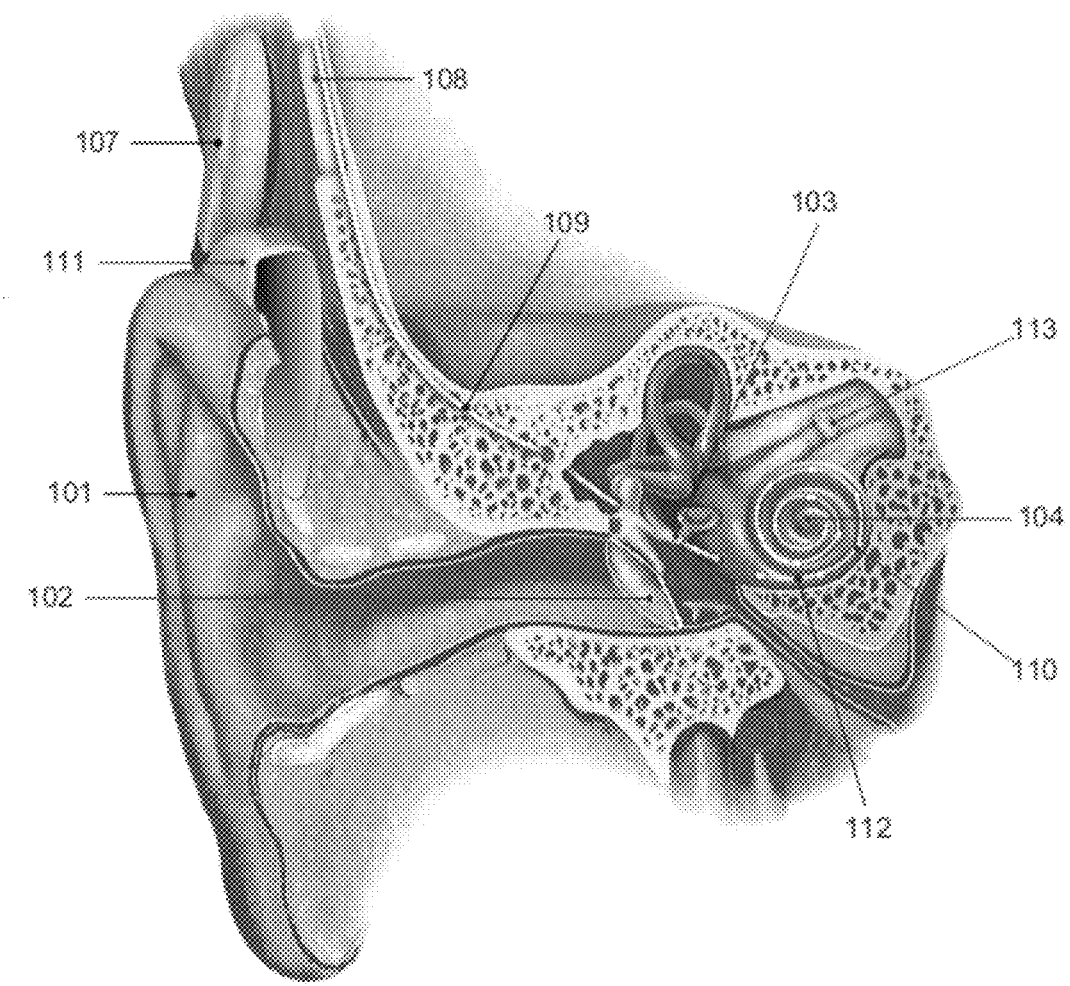
FIG. 1 shows anatomical structures of a human ear and some components of a typical cochlear implant system.
Figure 2:
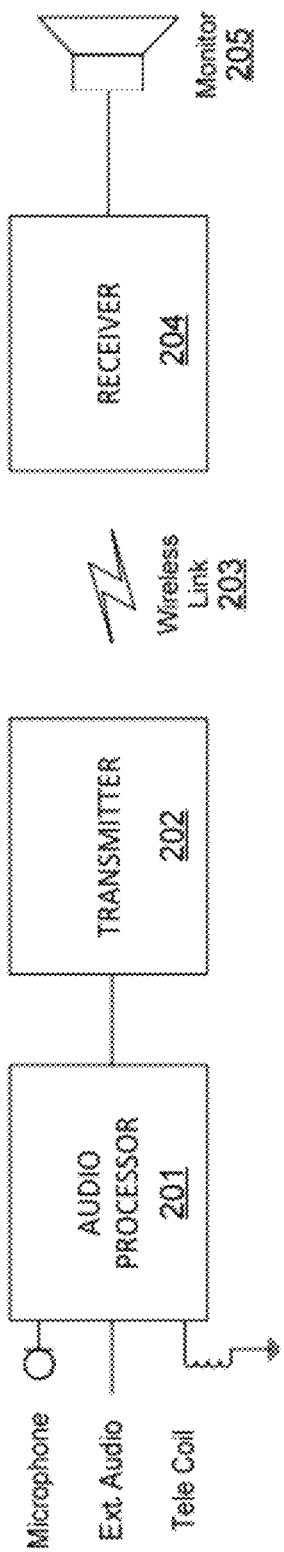
FIG. 2 shows various functional blocks in one specific embodiment of the present invention.

FIG. 2 shows various functional blocks in one specific embodiment of the present invention. An audio processor 201 receives an electrical audio input signal from one or more audio inputs such as a microphone signal, a telecoil signal, an external audio signal. In normal system operation, the audio processor 201 develops a corresponding implant stimulation signal output that is transmitted by a stimulation signal transmitter 202 over a wireless link 203 to an implanted portion of a hearing implant system such as a cochlear implant (CI) system, an auditory brainstem implant (ABI) system, or a middle ear implant (MEI) system.

The audio processor 201 includes an audio bypass mode which provides the audio input signal to the stimulation signal transmitter 202 for transmission over the wireless link 203 to a monitor receiver 204. This may occur, for example, in response to some pre-determined event such as the user operating a monitor check control on the body of the audio processor 201 or on its remote control, or when the audio processor 201 detects that it is no longer driving the implanted part of the hearing implant system. Of course, the audio bypass signal needs to be routed to the stimulation signal transmitter 202 in an appropriate format (e.g. analog, digital coded, etc.) for transmission and reception by the monitor receiver 204.

The monitor receiver 204 receives the audio bypass signals from the wireless link 203 and converts them into an electric audio signal corresponding to the internal electric audio signal inside the audio processor 201 (i.e., a restored audio signal). Unless already available in analog form, the restored audio signal is converted into an analog audio output signal to a user monitor 205 such as a headphone or loudspeaker which a normal hearing person can hear.

Such an arrangement removes the need for space consuming and mechanically fragile external connectors for checking the internal audio signal. Among other things, this allows the body of the external processor to be physically smaller. Moreover, it is easier for the user to handle since there is no need to plug a cable into a (usually) small connector on the outer body of the processor. Nor is there any need to disassemble the body of the audio processor to obtain access to monitor connectors.

Of course, while the normal hearing person listens to the audio bypass signal, the audio processor cannot be used to provide a stimulation signal for the hearing implant user. However, this should not be a significant drawback since this downtime of the hearing implant system should usually be very short. Also, depending on the actual implementation, the above described receiver might be more technically complex than a connector and a plug arrangement.

Note that such audio bypass monitoring should not be confused with other systems that may simulate the implanted part of the hearing implant system and that converts the signals (analog or digital) usually transmitted to the implanted part of the hearing implant system into acoustic audio signals a normal hearing person can listen to via a headphone or loudspeaker. On the one hand, the stimulation signals that are usually transmitted via the wireless link to the implanted part of the hearing implant system are always significantly processed and therefore do not fully represent the input audio signal. And on the other hand—more importantly—in certain hearing implant systems (e.g. cochlear implant systems) the normal transmitted stimulation signals are processed such that a restoration of the original picked up audio signal is simply not possible.

Embodiments of the invention may be implemented in whole or in part in any conventional computer programming language such as VHDL, SystemC, Verilog, ASM, etc. Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. An external processor device for a hearing implant system, the device comprising:
   an audio signal processor configured to receive an electrical input signal containing audio information received from an external microphone and to develop a corresponding implant stimulation signal output;
   a stimulation signal transmitter coupled to the signal processor and configured to receive the implant stimulation signal and transmit the implant stimulation signal to an implanted portion of the hearing implant system;
   wherein the device includes an audio bypass mode wherein the audio bypass mode provides the electrical input signal received from the external microphone to the stimulation signal transmitter for transmission instead of the implant stimulation signal.

2. A device according to claim 1, wherein the hearing implant system includes a cochlear implant (CI) system.

3. A device according to claim 1, wherein the hearing implant system includes an auditory brainstem implant (ABI) system.

4. A device according to claim 1, wherein the hearing implant system includes a middle ear implant (MEI) system.

* * * * *